United States Patent
Ooi et al.

(10) Patent No.: US 11,754,532 B2
(45) Date of Patent: Sep. 12, 2023

(54) BEETLE DETECTION USING OPTICAL FIBER DISTRIBUTED ACOUSTIC SENSOR

(71) Applicant: KING ABDULLAH UNIVERSITY OF SCIENCE AND TECHNOLOGY, Thuwal (SA)

(72) Inventors: Boon Siew Ooi, Thuwal (SA); Yuan Mao, Thuwal (SA); Islam Ashry, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 567 days.

(21) Appl. No.: 17/050,116

(22) PCT Filed: Apr. 24, 2019

(86) PCT No.: PCT/IB2019/053397
§ 371 (c)(1),
(2) Date: Oct. 23, 2020

(87) PCT Pub. No.: WO2019/234516
PCT Pub. Date: Dec. 12, 2019

(65) Prior Publication Data
US 2021/0096106 A1  Apr. 1, 2021

Related U.S. Application Data

(60) Provisional application No. 62/742,592, filed on Oct. 8, 2018, provisional application No. 62/695,299, filed
(Continued)

(51) Int. Cl.
*G01N 29/46* (2006.01)
*G01N 29/24* (2006.01)
(Continued)

(52) U.S. Cl.
CPC ......... *G01N 29/2418* (2013.01); *G01H 9/004* (2013.01); *G01N 29/4454* (2013.01);
(Continued)

(58) Field of Classification Search
CPC ............... G01N 33/46; G01N 33/0098; G01N 29/2418; G01H 9/004
See application file for complete search history.

(56) References Cited

U.S. PATENT DOCUMENTS

2009/0007670 A1   1/2009  Hawwa et al.
2016/0060734 A1   3/2016  Smarsly et al.
(Continued)

FOREIGN PATENT DOCUMENTS

FR   3025218 A1   3/2016
WO   2016124944 A1   8/2016
WO   2017096421 A1   6/2017

OTHER PUBLICATIONS

Bao, X., et al., "Recent Development in the Distributed Fiber Optic Acoustic and Ultrasonic Detection," Journal of Lightwave Technology, Aug. 15, 2017, vol. 35, No. 16, pp. 3256-3267, IEEE.
(Continued)

*Primary Examiner* — Maurice C Smith
(74) *Attorney, Agent, or Firm* — PATENT PORTFOLIO BUILDERS PLLC

(57) ABSTRACT

An optical fiber distributed acoustic sensor (DAS) system for detecting a red palm weevil and/or its larvae inside a tree. The system includes an optical fiber that is configured to be placed next to a tree; and a DAS box optically connected to the optical fiber and configured to receive a reflected light from the optical fiber. The DAS box includes electronics that extracts from the reflected light a frequency in a range of [400 Hz, 4 kHz], and sends a message indicating a presence of the red palm weevil and/or its larvae inside the tree.

20 Claims, 14 Drawing Sheets

Related U.S. Application Data on Jul. 9, 2018, provisional application No. 62/687,507, filed on Jun. 20, 2018, provisional application No. 62/680,677, filed on Jun. 5, 2018.

(51) Int. Cl.

| | |
|---|---|
| *G01H 9/00* | (2006.01) |
| *G01N 29/44* | (2006.01) |
| *G01N 33/00* | (2006.01) |
| *A01M 99/00* | (2006.01) |
| *G01N 33/46* | (2006.01) |

(52) U.S. Cl.
CPC ......... *G01N 29/46* (2013.01); *G01N 33/0098* (2013.01); *A01M 99/00* (2013.01); *G01N 33/46* (2013.01); *G01N 2291/0238* (2013.01)

(56) References Cited

U.S. PATENT DOCUMENTS

| | | |
|---|---|---|
| 2016/0238376 A1 | 8/2016 | Ohtsuka |
| 2016/0258795 A1 | 9/2016 | Farhadiroushan et al. |

OTHER PUBLICATIONS

El-Mergawy, R.A.A.M., et al., "Red Palm Weevil, Rhynchophorus ferrugineus (Olivier): Economic Importance, Biology, Biogeography and Integrated Pest Management," Journal of Agricultural Science and Technology A 1, May 20, 2011, pp. 1-23, David Publishing.

Gutierrez, A., et al., "Development of a Bioacoustic Sensor for the Early Detection of Red Palm Weevil (Rhynchophorus Ferrugineus Olivier)," Jul. 1, 2010, vol. 29, No. 7, pp. 671-676, Elsevier Science, GB.

Haff, R.P., et al., "Real-Time X-Ray Inspection of Wheat for Infestation by the Granary Weevil, *Sitophilus granarius* (L.)," Transactions of the ASAE, Mar. 2004, vol. 47, No. 2, pp. 531-537.

Hussein, W.B., et al., "Detection of the Red Palm Weevil Rhynchophorus Ferrugineus using its Bioacoustics Features," Bioacoustics, The International Journal of Animal Sound and its Recording, Apr. 13, 2012, vol. 19, pp. 177-194, AB Academic Publishers.

International Search Report in corresponding/related International Application No. PCT/IB2019/053397, dated Aug. 16, 2019.

Juarez, J.C., et al., "Field Test of a Distributed Fiber-Optic Intrusion Sensor System for Long Perimeters," Applied Optics, Apr. 10, 2007, vol. 46, No. 11, pp. 1968-1971.

Mankin, R.W., "Recent Developments in the sue of Acoustic Sensors and Signal Processing Tools to Target Early Infestations of Red Palm Weevil in Agricultural Environments," Florida Entomologist, Dec. 2011, vol. 94, No. 4, pp. 761-765.

Mao, Y., et al., "Towards Early Detection of Red Palm Weevil using Optical Fiber Distributed Acoustic Sensor," 2019 Optical Fiber Communications Conference and Exhibition (OFC), USA, Mar. 3, 2019, pp. 1-3.

Merlo, S., et al., "Runways Ground Monitoring System by Phase-Sensitive Optical-Fiber OTDR," 2017 IEEE International Workshop on Metrology for AeroSpace (MetroAeroSpace), Padua, Jun. 21-23, 2017, pp. 523-529.

Mukhtar, M., et al., "New Initiatives for Management of Red Palm Weevil Threats to Historical Arabian Date Palms," Florida Entomologist, Dec. 2011, vol. 94, No. 4, pp.733-736.

Rach, M.M., et al., "On the Design of a Bioacoustic Sensor for the Early Detection of the Red Palm Weevil," Sensors, Jan. 30, 2013, vol. 13, No. 2, pp. 1706-1729.

Siriwardena, K.A.P., et al., "Portable Acoustic Device for Detection of Coconut Palms Infested by Rynchophorus Ferrugineus (Coleoptera: Curculionidae)," Crop Protection, Jan. 2010, vol. 29, pp. 25-29, Elsevier Ltd.

Suma, P., et al., "The use of Sniffing Dogs for the Detection of Rhynchophorus Ferrugineus," Phytoparasitica, Aug. 14, 2013, vol. 42, pp. 269-274, Springer.

Written Opinion of the International Searching Authority in corresponding/related International Application No. PCT/IB2019/053397, dated Aug. 16, 2019.

Yamate, T., et al., "Optical Sensors for the Exploration of Oil and Gas," Journal of Lightwave Technology, Aug. 15, 2017, vol. 35, No. 16, pp. 3538-3545.

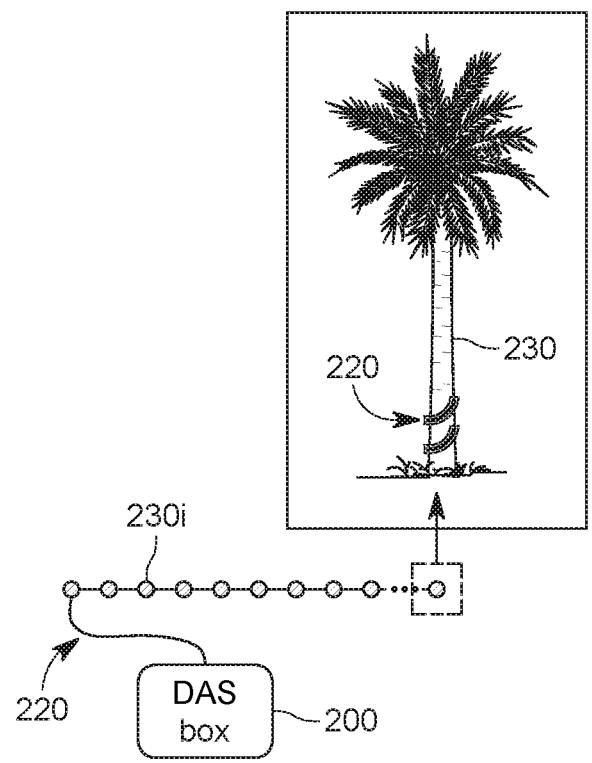
FIG. 3A
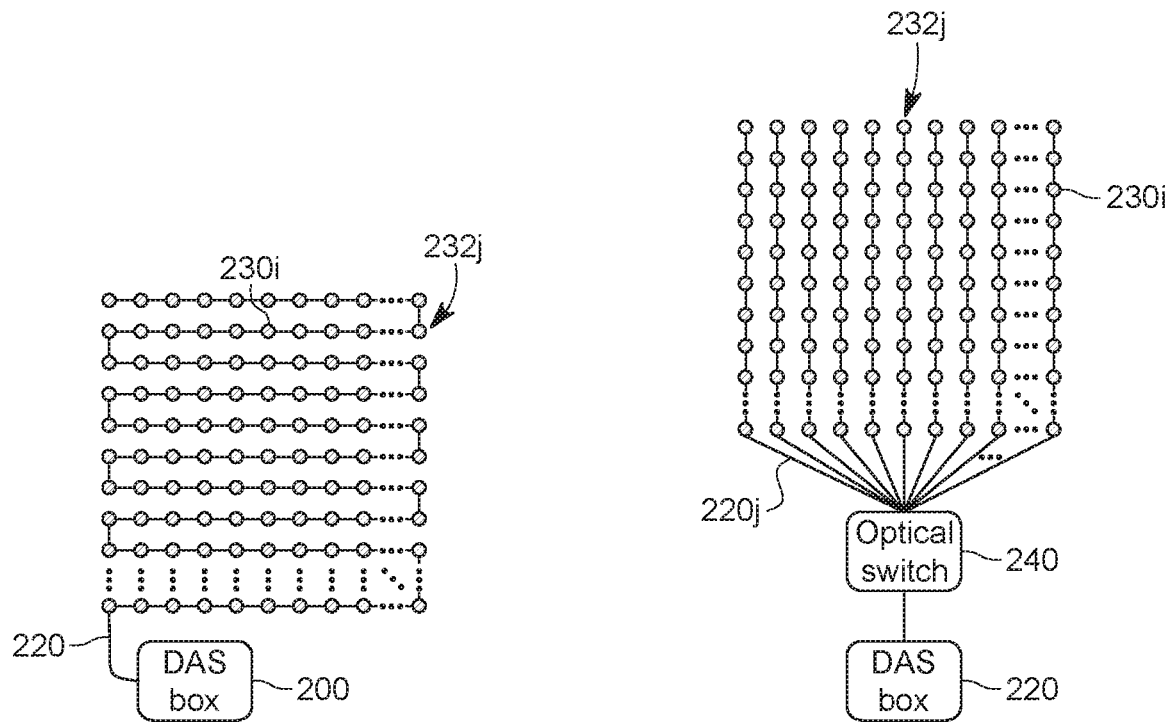
FIG. 3B
FIG. 3C

BEETLE DETECTION USING OPTICAL FIBER DISTRIBUTED ACOUSTIC SENSOR

CROSS-REFERENCE TO RELATED APPLICATIONS

This application is a U.S. National Stage Application of International Application No. PCT/IB2019/053397, filed on Apr. 24, 2019, which claims priority to U.S. Provisional Patent Application No. 62/680,677, filed on Jun. 5, 2018, entitled "EARLY DETECTION OF THE RED PALM WEEVIL USING OPTICAL FIBER DISTRIBUTED ACOUSTIC SENSOR," U.S. Provisional Patent Application No. 62/687,507, filed on Jun. 20, 2018, entitled "EARLY DETECTION OF THE RED PALM WEEVIL USING OPTICAL FIBER DISTRIBUTED ACOUSTIC SENSOR," and U.S. Provisional Patent Application No. 62/695,299, filed on Jul. 9, 2018, entitled "BEETLE DETECTION USING OPTICAL FIBER DISTRIBUTED ACOUSTIC SENSOR," and U.S. Provisional Patent Application No. 62/742,592, filed on Oct. 8, 2018, entitled "TOWARDS EARLY DETECTION OF RED PALM WEEVIL USING OPTICAL FIBER DISTRIBUTED ACOUSTIC SENSOR," the disclosures of which are incorporated herein by reference in their entirety.

BACKGROUND

Technical Field

Embodiments of the subject matter disclosed herein generally relate to a system and method for detecting the presence of a beetle and its larvae in a tree, and more specifically, using an optical fiber distributed acoustic sensor for early detection of the beetle and its larvae in a palm tree.

Discussion of the Background

Red Palm Weevil beetle and its larvae, herein referring to RPW, is considered one of the most serious threats to palm agriculture in many countries around the world. Curative techniques for such insect are not difficult to apply. However, early detection of the RPW is the centerpiece challenging hurdle. This is so because palm trees show visual infection symptoms too late, when it is almost impossible to treat and heal them. Consequently, developing a method for reliable and efficient early detection of the RPW presence inside the tree is required for RPW pest control.

Several techniques have been reported in the literature to tackle this problem. For example, a computer-based tomography system was used to screen infested trees (see, Haff, R. P., "Real-time X-ray inspection of wheat for infestation by the granary weevil, Sitophilus granarius (L)," Trans. ASAE 2003, 47, 531-537). However, this method lacks applicability since it is very expensive and requires sophisticated power supplies.

Other techniques focused on sensing the gases generated during the fermentation processes in the infected palms by using, for instance, trained dogs (Suma, P.; La Pergola, A.; Longo, S.; Soroker, V., "The use of sniffing dogs for the detection of Rhynchophorus ferrugineus," Phytoparasitica 2014, 42, 269-274.). Unfortunately, the sniffing dogs are not selective and their results are impacted by many other volatiles.

The most promising RPW early detection techniques are based on acoustic sensors (see, Rach, M. M; Gomis, H. M; Granado, O. L; Malumbres, M. P.; Campoy, A. M.; Martin, J. J. S., "On the Design of a Bioacoustic Sensor for the Early Detection of the Red Palm Weevil," 2013, 13, 1706-1729, also see Gutiérrez, A.; Ruiz, V.; Moltó, E.; Tapia, G.; Téllez, M. del M., "Development of a bioacoustic sensor for the early detection of red palm weevil (rhynchophorus ferrugineus olivier)," Crop Prot. 2010, 29, 671-676, or Siriwardena, K. A. P.; Fernando, L. C. P.; Nanayakkara, N.; Perera, K. F. G.; Kumara, A. D. N. T.; Nanayakkara, T., "Portable acoustic device for detection of coconut palms infested by rynchophorus ferrugineus (coleoptera: curculionidae)," Crop Prot. 2010, 29, 25-29, or Hussein, W. B.; Hussein, M. A.; Becker, T., "Detection of the red palm weevil rhynchophorus ferrugineus using its bioacoustics features," Bioacoustics 2010, 19, 177-194, or Mankin, R. W. "Recent developments in the use of acoustic sensors and signal processing tools to target early infestations of red palm weevil in agricultural environments," Fla. Entomol. 2011, 94, 761-765). This is because the sound associated with the RPWs activities within the palm trunk can be heard by humans, under reasonable noise levels. Furthermore, the frequency components of the RPW generated sound are within 400-2500 Hz band, which can easily be spectrally separated from the acoustic noise signals of typical frequencies less than 100 Hz.

The existing methods that use acoustic sensors, as illustrated in FIG. 1, primarily insert an acoustic probe 102, such as microphone, in a hole 104 made in a palm trunk 106 and then they record the sound produced by the beetles in real-time. The sound is recorded on a computer 108 that is connected to the acoustic probe 102. The differences among these methods are mainly in the signal processing techniques implemented for processing the recorded sound. However, all these methods require in-situ monitoring.

For vast farms, checking palms one-by-one is labor-, time-, and cost-consuming. Moreover, a major drawback of these reported methods is that they do not offer continuous monitoring for palm trees. An alternative solution is disclosed by Rach (see above), where each palm is equipped with a corresponding sound probe, which is connected to a wireless communication interface so that data transfer can take place to a central server. The system is powered via a solar panel. Although this method provides continuous observation for the individual palm trees, its overall cost is very high. Another disadvantage of the aforementioned acoustic methods is the damage done to the tree because inserting a sound probe into a palm might be hard, impact the growth of palms, and create a nest for other insects, after removing it.

Thus, there is a need for a new method and system that is not limited by the above drawbacks of the existing methods.

SUMMARY

According to an embodiment, there is an optical fiber distributed acoustic sensor (DAS) system for detecting a red palm weevil and/or its larvae inside a tree. The system includes an optical fiber that is configured to be placed next to a tree; and a DAS box optically connected to the optical fiber and configured to receive a reflected light from the optical fiber. The DAS box includes electronics that extracts from the reflected light a frequency in a range of [400 Hz, 4 kHz], and sends a message indicating a presence of the red palm weevil and/or its larvae inside the tree.

According to another embodiment, there is a method for detecting a red palm weevil inside a tree. The method includes a step of deploying an optical fiber next to a tree; a step of optically connecting a DAS box to the optical fiber;

a step of receiving a reflected light from the optical fiber, wherein the reflected light contains information about a sound generated by the red palm weevil; a step of processing with electronics in the DAS box the reflected light, to extract a frequency in a range of [400 Hz, 4 kHz], which is indicative of the red palm weevil; and a step of sending a message indicating a presence of the red palm weevil inside the tree.

BRIEF DESCRIPTION OF THE DRAWINGS

The accompanying drawings, which are incorporated in and constitute a part of the specification, illustrate one or more embodiments and, together with the description, explain these embodiments. In the drawings:

FIG. 3A illustrates the use of a single optical fiber for a plurality of trees arranged in a line, FIG. 3B illustrates the use of a single optical fiber for plural lines of trees, and FIG. 3C illustrates the use of plural optical fibers for plural lines of trees;

DETAILED DESCRIPTION

The following description of the embodiments refers to the accompanying drawings. The same reference numbers in different drawings identify the same or similar elements. The following detailed description does not limit the invention. Instead, the scope of the invention is defined by the appended claims. For simplicity, the following embodiments are discussed with regard to detecting the RPW inside a tree. However, the embodiments are not limited to this specific case and one skilled in the art would understand that the same embodiments can be used to detect other insects or bugs, outside of a tree.

Reference throughout the specification to "one embodiment" or "an embodiment" means that a particular feature, structure or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

According to an embodiment, a novel system and method for early detection of RPW uses an optical fiber distributed acoustic sensor (DAS). Optical fiber DAS is essentially designed using phase-sensitive optical time domain reflectometry ($\phi$-OTDR), which has been utilized in many potential applications such as oil and gas industry, real-time structural health monitoring, and aerospace transportation.

The underlying operation concept of an optical fiber DAS relies on using a coherent (narrow linewidth) laser source to launch optical pulses into a fiber. While a pulse is propagating along the fiber, a Rayleigh trace is backscattered from the fiber and it is recorded at the fiber input port. By monitoring the intensity's temporal evolution of the recorded Rayleigh traces, it is possible to accurately calculate a position along the fiber, which was subjected to an acoustic signal and to determine its frequency. If the frequency belongs to the range of frequencies emitted by the RPW, then it is determined that the RPW is present in the tree.

Figure 1:
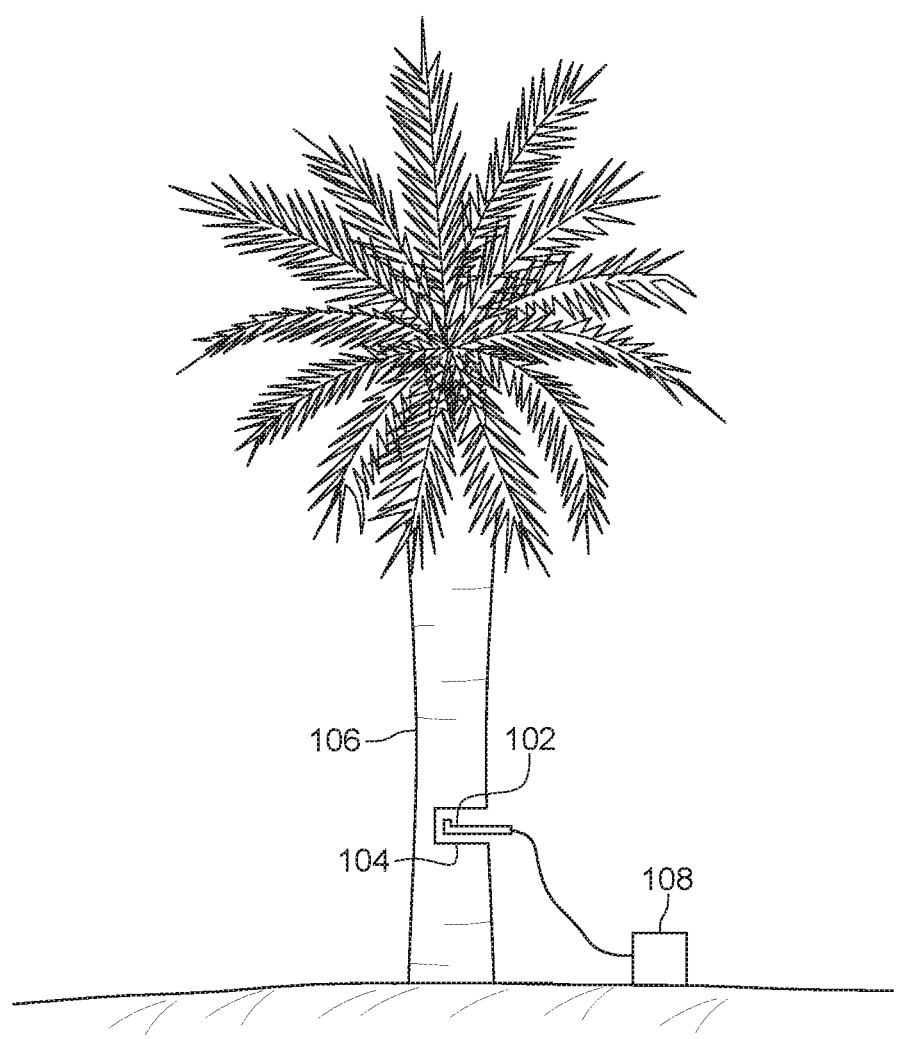
FIG. 1 is a schematic illustration of a traditional system for detecting the RPW in a tree.
Figure 2:
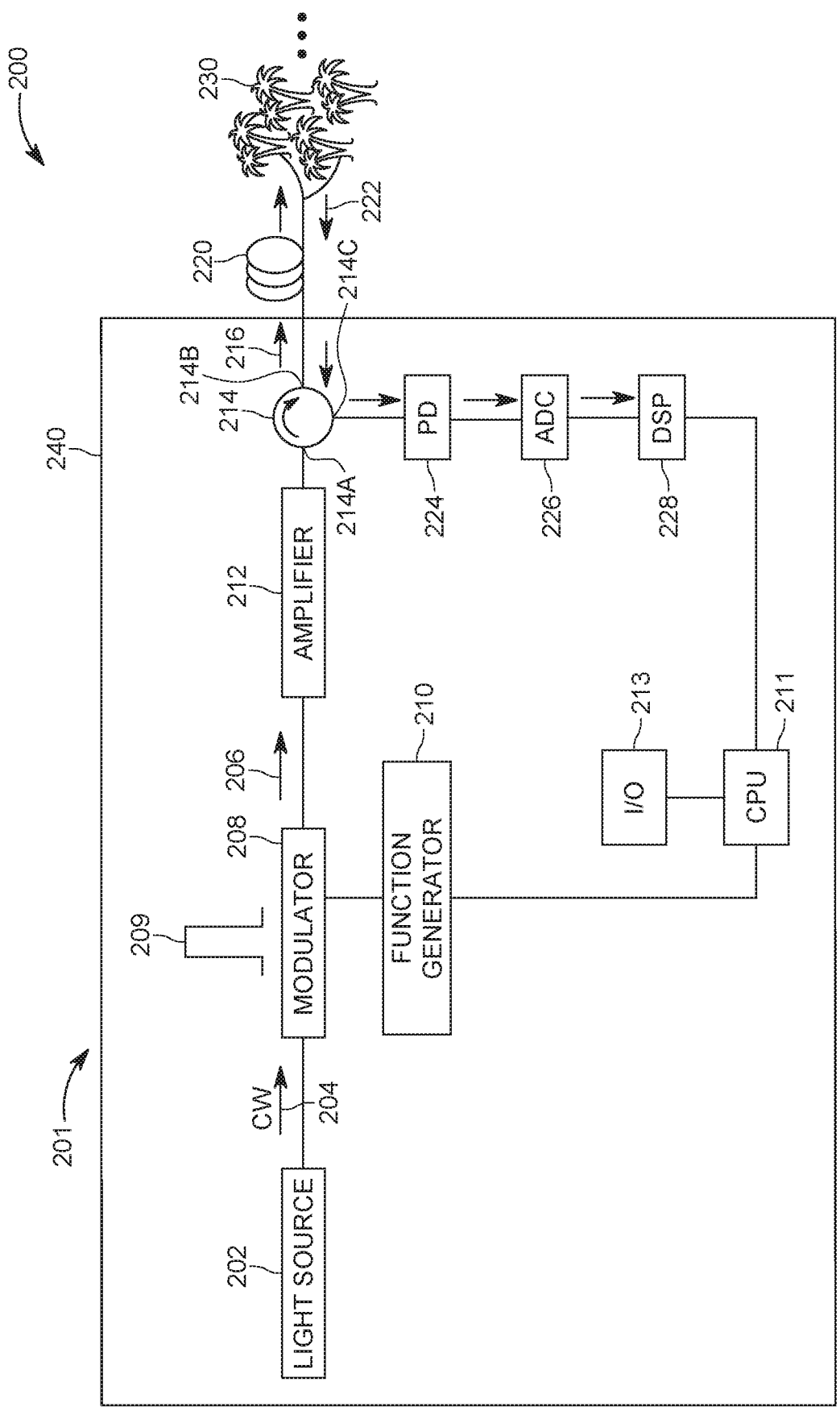
FIG. 2 illustrates an optical fiber distributed acoustic sensor system for detecting the presence of the RPW.

In this regard, FIG. 2 shows a fiber optic DAS system 200 that is capable of measuring a strain exerted on the optical fiber by changes in pressure, temperature and/or acoustic noise. System 200 has two main components, a DAS box 201 and the optical fiber 220. The DAS box 201 includes all the electronics for generating a light, sending the light to the optical fiber, receiving a reflected light from the optical fiber, and processing the reflected light for detecting the RPW. More specifically, the DAS box 201 includes a light source 202 that is configured to generate continuous-wave (CW) light 204 that is coherent. For example, the light source 202 may be a laser. The CW light 204 is converted to optical pulses 206 via a light modulator 208. The light modulator 208 is connected to a function generator 210. The function generator 210, which can be controlled by a computing device 211, is configured to generate a mathematical function to be applied to the modulator to modulate the light 204. For example, FIG. 2 shows the modulator 208 applying a rectangular pulse 209 to the light 204, to obtain the optical pulses 206 (or modulated light). The computing device 211 is also connected to an input/output module 213, which is capable of communicating, for example, in a wireless or wired manner with a smartphone, personal computer, or any other electronic device for both sending messages and also for receiving instructions.

Optionally, the system 200 includes an amplifier 212 for amplifying the modulated light 206, prior to launching it through a circulator 214 into the optical fiber 220. FIG. 2 schematically shows the optical fiber 220 being directed to plural trees 230. The way in which the optical fiber 220 is attached to trees is discussed later. The circulator 214 may be, for example, a three- or four-port optical device designed such that light entering any port exits from the next port. This means that if light enters a first port 214A, it is emitted from a second port 214B. However, if some of the emitted light 216 is reflected back to the circulator 214, it does not come out of the first port 214A, but instead exits from a third port 214C. This makes possible that a reflected Rayleigh signal 222, after reaching the circulator 214, is directed toward a photodetector 224, instead of being sent toward the amplifier 212.

While the optical pulse 216 is propagating along the fiber 220, the Rayleigh signal 222 is backscattered from the fiber 220. In the backward direction, the Rayleigh signal is recorded via the photodetector 224 and then sampled using an analog-to-digital converter (ADC) 226. A digital signal processing (DSP) 228 may be used to filter out the RPW sounds in the frequency domain and exactly identifies the locations of the infected palm trees 230 using, for example, the time domain signal.

By monitoring the intensity temporal evolution of the recorded Rayleigh signals 222, one can accurately figure out a position along the optical fiber 220 which was subjected to an acoustic signal emitted by the RPW and thus, determine the location of the RPW. For the purpose of RPW early detection, the system 200 shown in FIG. 2 outweighs the existing acoustic sensors in the literature because of at least one of the following reasons: 1) it would provide non-stop monitoring for palm trees with a relatively low price, 2) the sensing length of the typical optical fiber DAS is around 10 km, which could cover spacious farm area, 3) by using an optical switch and time-division-multiplexing (TDM), several fibers can be attached to the same DAS box, in case that monitoring larger farm areas is demanded, 4) no invasive sensing is required since the optical fiber would be wounded externally around the palms, and 5) the optical fiber used for acoustic sensing can simultaneously monitor ambient temperatures, with a resolution less than 0.1° C., which is considerably important to control farm fires, which is another major problem around the world.

In one embodiment, all the elements of the system 200, except the optical fiber 220, may be placed in a single housing 240, called herein the DAS box. This means that all of the optical components such as laser, photodetector, etc., are gathered within the DAS box, for example, at a control master station, whereas only the optical fiber 220 is wounded around the palm trees 230 in a form of optical network.

The optical fiber 220 can be distributed along one or more trees. For example, FIG. 3A shows an embodiment in which the DAS box 200 is connected to a single optical fiber 220, which extends at plural trees 230i, where i is any natural number. The same optical fiber 220 can be rolled around each tree 230i. In another embodiment illustrated in FIG. 3B, a single DAS box 200 and a single optical fiber 220 are used to monitor plural trees 230i. However, in this embodiment, the trees are not just a line of trees as in the embodiment of FIG. 3A, but plural lines 232j of trees, with j being a natural number. Note that in this embodiment, the same optical fiber 220 extends along each line 232j of trees 230i.

In yet another embodiment illustrated in FIG. 3C, plural optical fibers 220j are distributed from a single DAS box 200, to plural lines 232j of trees 230i. An optical switch 240 may be used to connect each optical fiber 220j to a corresponding line 232j of trees 230i. The optical switch 240 may be programmed to connect each optical fiber 220j, for a given time, to the DAS box 220, enough to get information to determine whether RPW are present in the trees or not. In this regard, note that there is no need to monitor the entire day a line of trees or a single tree for determining that RPW are present. Intermittent monitoring of the trees, for example, every hour or every couple of hours or even every day or every couple of days could be enough for determining the RPW presence.

Thus, the topology of the optical fiber DAS network, as illustrated in FIGS. 3A to 3C is quite flexible and can be adapted to fit almost any spatial distribution of palm trees. If the sum of the separations between consecutive trees, including the lengths of the optical fibers wounded around trees, is within the sensing range of the DAS system 200, one optical fiber is sufficient to cover the whole farm, as illustrated in FIGS. 3A and 3B. Otherwise, for extremely large farms, multiple fibers 220j can be connected through an optical switch to the DAS box, as illustrated in FIG. 3C. Because the sensing speed is not a considerable factor in this application, rotating the optical switch 240 around the different fibers 230j would provide continuous monitoring to the whole trees.

Figure 4:
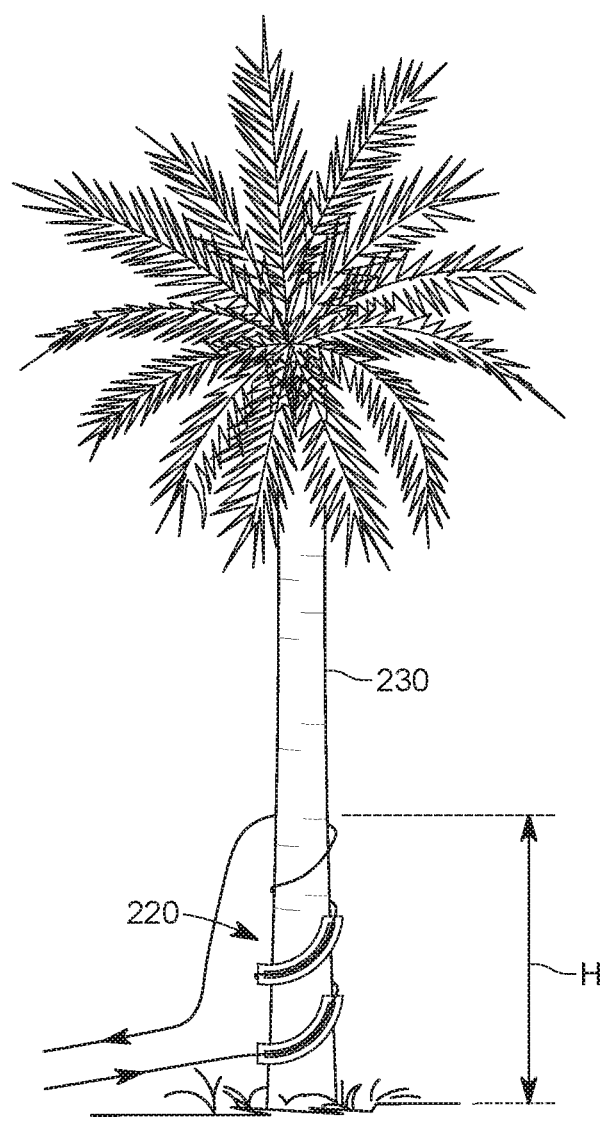
FIG. 4 illustrates how a portion of an optical fiber is placed around a tree.

A representative example for winding the optical fiber 220 around a tree 230 is shown in FIG. 4. The optical fiber 220 is looped around the trunk of tree 230, from the ground level up to a height H, and then the optical fiber is brought back to the ground level and rolled to the next tree.

Figure 5:
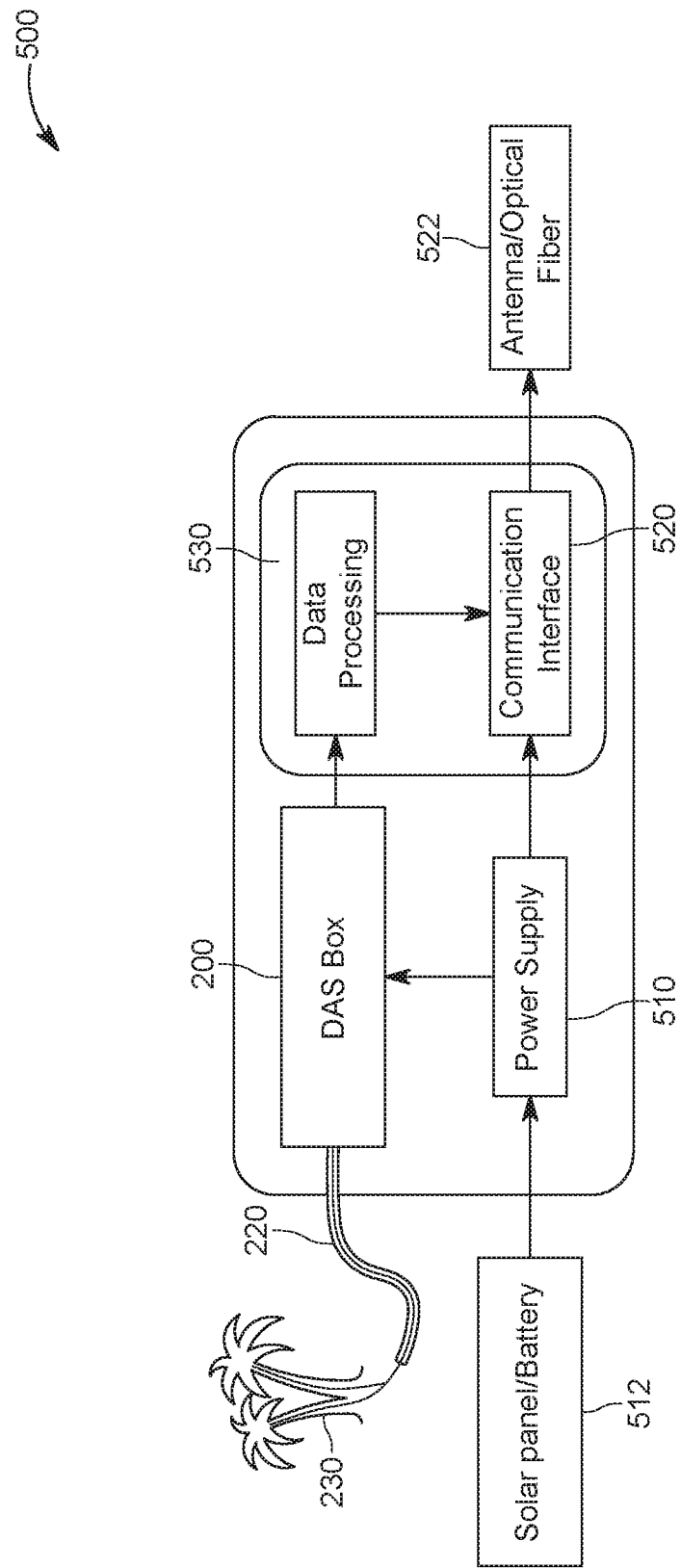
FIG. 5 illustrates an autonomous optical fiber DAS system.

In remote areas, the DAS system 200 can be a stand-alone system, as illustrated in FIG. 5. In this case, a stand-alone system 500 includes the DAS box 200, a power supply 510, a communication interface 520, and a data processing module 530. The power supply 510 may be connected to a solar panel or battery unit 512. The power supply 510 may include electronics for providing a constant voltage to the DAS box 200. The communication interface 520 is configured to communicate with the power supply 510, the DAS box 200, and the data processing module 530. In one application, the communication interface 520 is connected to an antenna or optical fiber 522 to communicate with a master controller or another system 500. Antenna 522 may be adapted for wireless communication. The data processing module 530 receives the data collected by the DAS box 200 and processes the data to determine the presence and/or location of the RPWs. The processed data can be either transmitted wirelessly or through an optical fiber 522 to the central controller.

Figure 6:
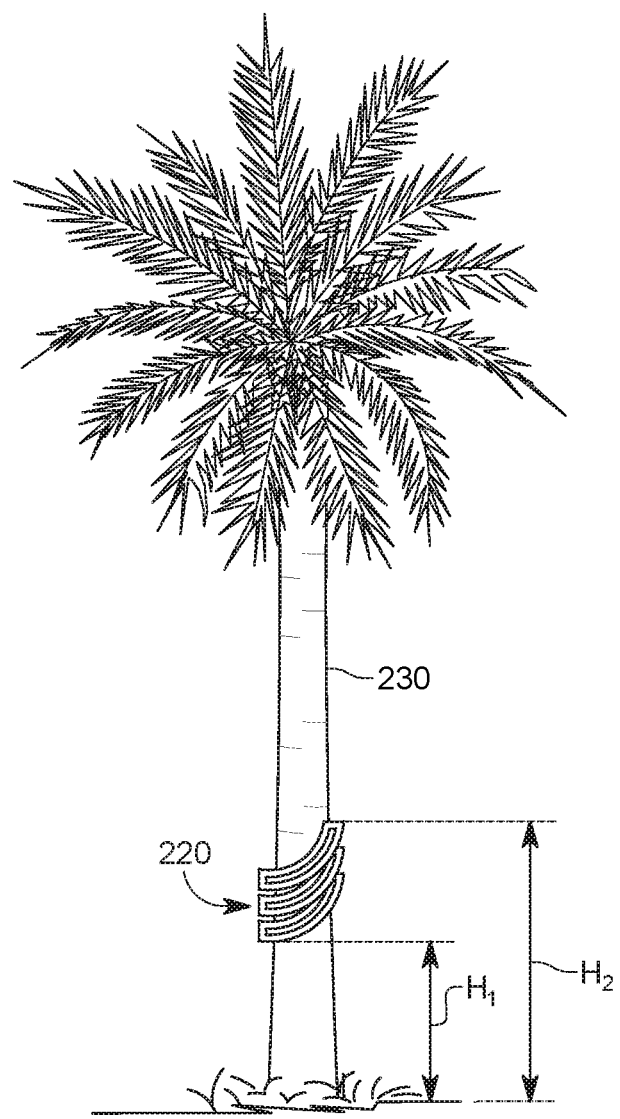
FIG. 6 illustrates how an optical fiber is selectively placed at a certain height relative to a tree.
Figure 7:
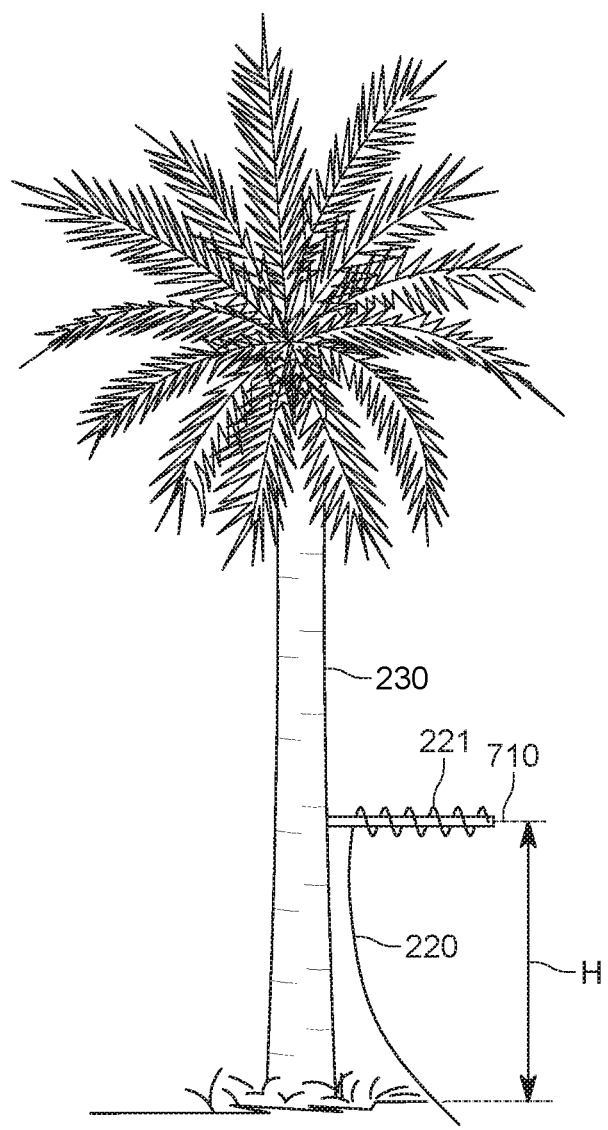
FIG. 7 shows another way of placing the optical fiber next to a tree.

Based on studies found in the literature (see, for example, Dembilio, O.; Jaques, J. A., "Biology and management of red palm weevil," *Sustainable Pest Management in Date Palm: Current Status and Emerging Challenges*. Springer, Cham, 2015. 13-36.), RPWs are more likely to attack palms at a meter above the ground. Thus, to increase the RPW detection probability, two different techniques for winding/attaching the optical fiber around/into a tree trunk are now discussed. According to an embodiment illustrated in FIG. 6, the optical fiber 220 is wound around the trunk of a tree 230 such that only a length L (e.g., about 1-25 m) of the optical fiber is present around each individual tree trunk, and this portion is located at a height H from the ground, in a range defined by two values H1 and H2. In one application, H1 is about 0.5 m and H2 is about 2 m. In another embodiment, as illustrated in FIG. 7, a length L of the optical fiber (e.g., 1-50 m section) 220 is first wound around a metallic rod 710 to create an optical fiber spool 221. Then, the rod 710 with the optical fiber 220 is implanted into the tree trunk 230 at a given height H (e.g., −1 m) from the ground.

Irrespective of which implementation of the optical fiber DAS system is selected, the method for detecting the RPW determines a certain range of sound, which is believed to be associated with one or more activities produced by the RPW. In this regard, the activities of the RPW larvae produce sound waves of frequencies within the interval [1 kHz, 4 kHz]. The adult weevils, on the other hand, generate sound waves having frequencies within the interval [400 Hz, 3 kHz]. Other values may be used, for example, about the 600 Hz, within a range of +1-10 or 20%. To fully extract the sound information related to the RPWs and discard any other noisy signals, during the signal processing that takes placed in DSP unit 228, it is possible to use a bandpass filter that covers the [400 Hz, 4 kHz] frequency range. Those skilled in the art would know how to program a DSP in order to remove other frequencies. When a frequency in the frequency range of [400 Hz, 4 kHz] is determined, the processor 211 would send an alarm, for example, a message through I/O unit 213, to a smartphone or another electronic device for indicating the presence of the RPWs.

In one embodiment, if the sum of the separations between consecutive trees, including the lengths of the fibers wounded around trees, is within the sensing range of the DAS system, one optical fiber is sufficient to cover the entire farm, as illustrated in FIG. 3B. Otherwise, for vast farms monitoring, time-division-multiplexing (TDM) can be used as shown in FIG. 3C. In particular, multiple optical fibers can be connected through an optical switch to the DAS box. For each optical fiber having a length less than 5 km, it is possible to assign a one-hour time slot to record the backscattered Rayleigh signals. Using the optical switch 240 discussed with regard to the embodiment illustrated in FIG. 3C, it is possible to sequentially collect data from plural individual optical fibers.

Figure 8:
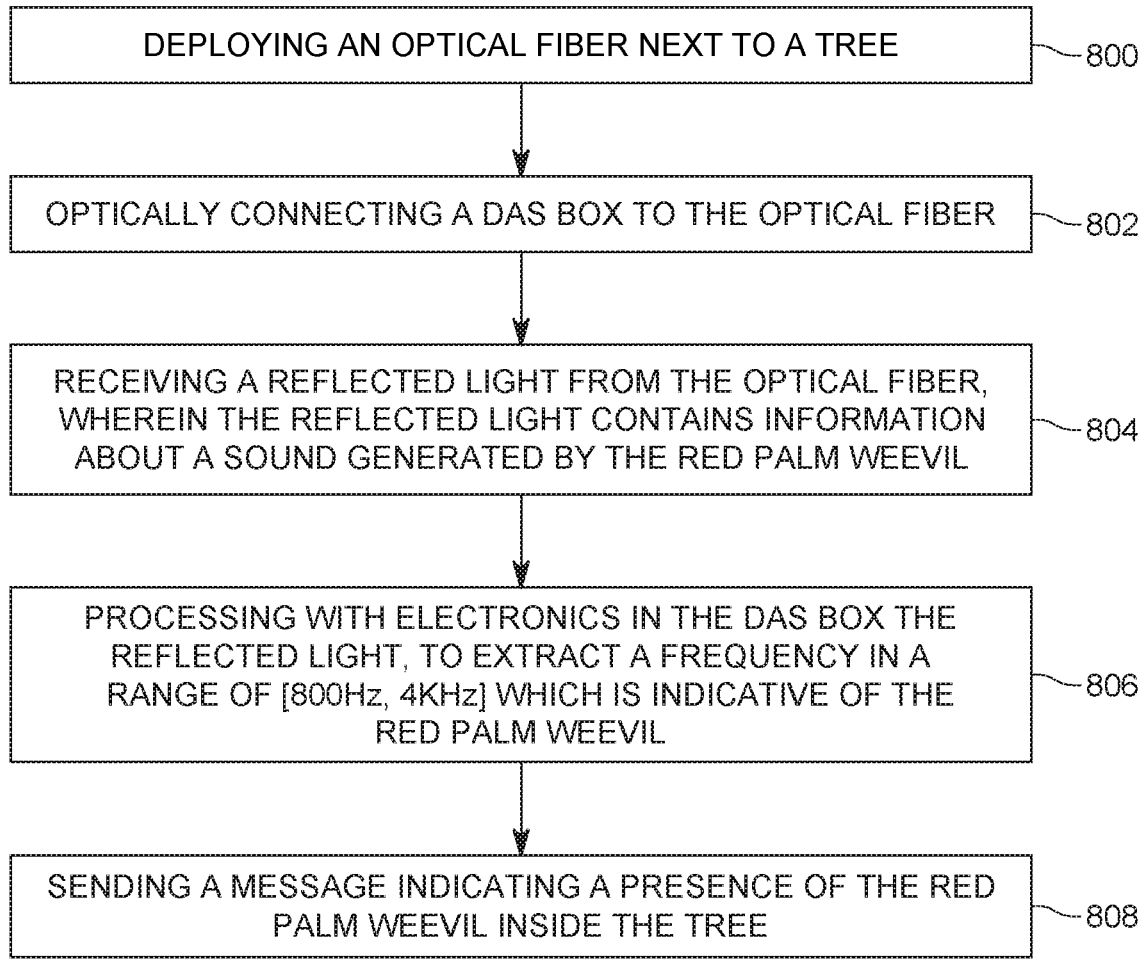
FIG. 8 is a flowchart of a method for determining the presence of the RPW in a tree.

A method for detecting the presence of RPWs is now discussed with regard to FIG. 8. The method includes a step 800 of deploying an optical fiber 220 next to a tree, a step 802 of optically connecting a DAS box 201 to the optical fiber 220, a step 804 of receiving a reflected light 222 from the optical fiber 220, wherein the reflected light contains information about a sound generated by the red palm weevil, a step 806 of processing with electronics in the DAS box 201 the reflected light 222, to extract a frequency in a range of [400 Hz, 4 kHz], which is indicative of the red palm weevil, and a step 808 of sending a message indicating a presence of the red palm weevil inside the tree.

Figure 9:
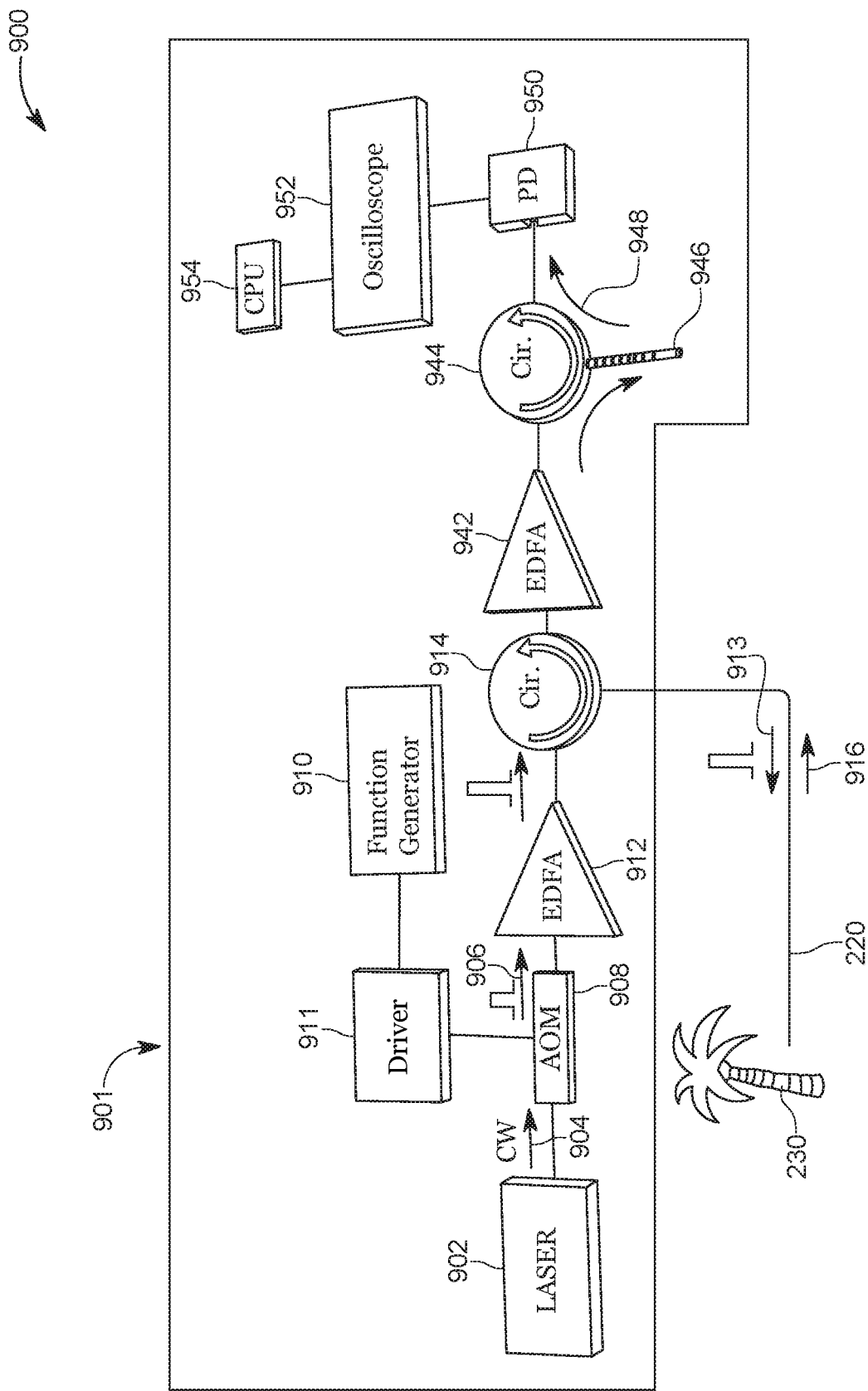
FIG. 9 illustrates another optical fiber distributed acoustic sensor system for detecting the presence of the RPW.

The DAS box 201 discussed with regard to FIG. 2 may also be implemented as illustrated in FIG. 9. DAS box 901 uses a narrow linewidth laser 902 that generates continuous-wave (CW) light 904 at 1535 nm operation wavelength. The laser light 904 is then converted into optical pulses 906 via an acousto-optic modulator (AOM) 908. The AOM 908 is driven by a function generator 910 and a driver 911. The repetition rate of the optical pulses is 20 kHz in this embodiment, and each pulse is 100 ns width, which offers 10 m sensing spatial resolution. The modulated optical pulses 906 are amplified using a first erbium doped fiber amplifier (EDFA) 912 and then launched through a first circulator 914 into a ~2.1 km standard single mode fiber (SMF) 220.

While an amplified optical pulse 913 is propagating along the SMF 220, Rayleigh signals 916 are continuously backscattered from the tree 230, along the fiber length. The backscattered Rayleigh signals 916 are firstly amplified using a second amplifier EDFA 942. The Rayleigh signals 916 are then directed to a second circulator 944, which distributes them to a fiber Bragg grating (FBG) 946. The fiber Bragg grating 946 filters out the amplified spontaneous emission (ASE) noise of the Rayleigh signals 916 to generate filtered Rayleigh traces 948. The filtered Rayleigh traces 948 are then recorded via a photodetector (PD) 950, sampled using an oscilloscope 952, and then processed, for example, at a processor 954, to extract the sensing information.

In one practical implementation of the configuration of FIG. 9, a 10 m fiber section was placed around a palm trunk while the remaining of the SMF was not in contact with the palm trunk. As representative examples during the experiments, the location of this section along the SMF length was changed. In particular, the experiments were carried out when the fiber section is located at about 110 m (denoted as "P1") or about 2100 m (denoted as "P2") distance from the SMF front facet. The sound associated with the RPW activities was played through a first loudspeaker, which is completely inserted into the core of the palm trunk. At about 1 m distance from the tree, a second loudspeaker and a stand fan were placed. The second speaker continuously produces birds sound while the fan rotates at about 1100 rpm speed and it is directed towards the tree to keep it swinging. The second loudspeaker and the fan were used to generate environmental noise to test how sensitive is the configuration of FIG. 9 to the medium. The sound volume of the second loudspeaker was tuned up until it produces birds sound with strength roughly equal to that a person would hear in a farm. On the other hand, because the RPW associated sound can be heard by humans in reasonable noisy environment, the volume of the first speaker was adjusted until its sound was clearly identified in the noisy environment.

Figure 10A:
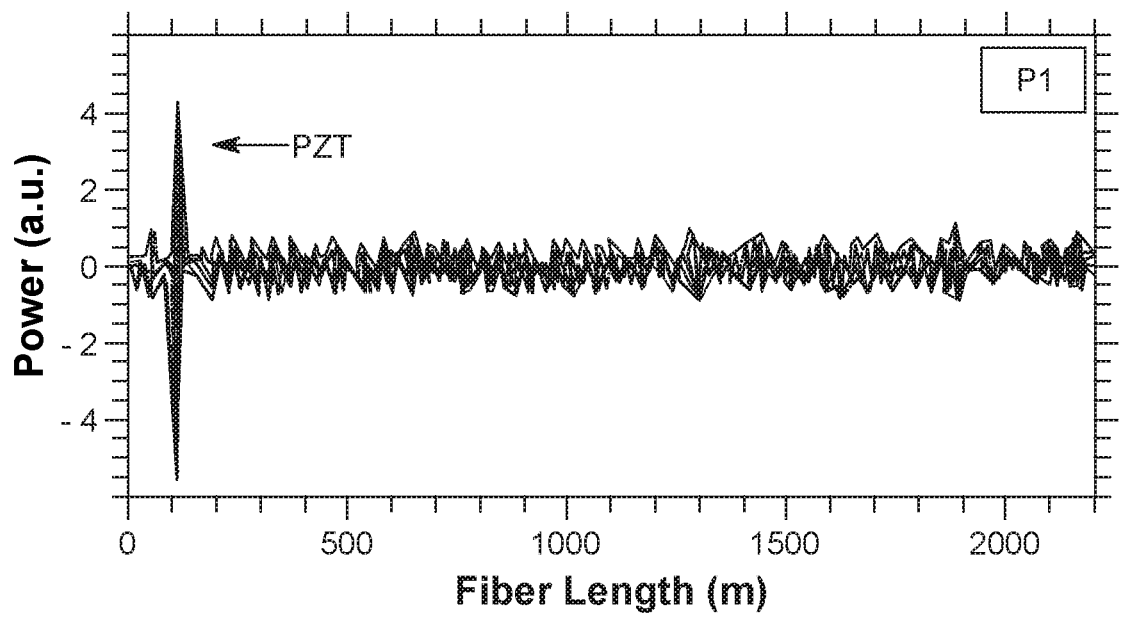
FIGS. 10A to 10H illustrate a power spectrum and frequency detected with the optical fiber distributed acoustic sensor system under various conditions.
Figure 10B:
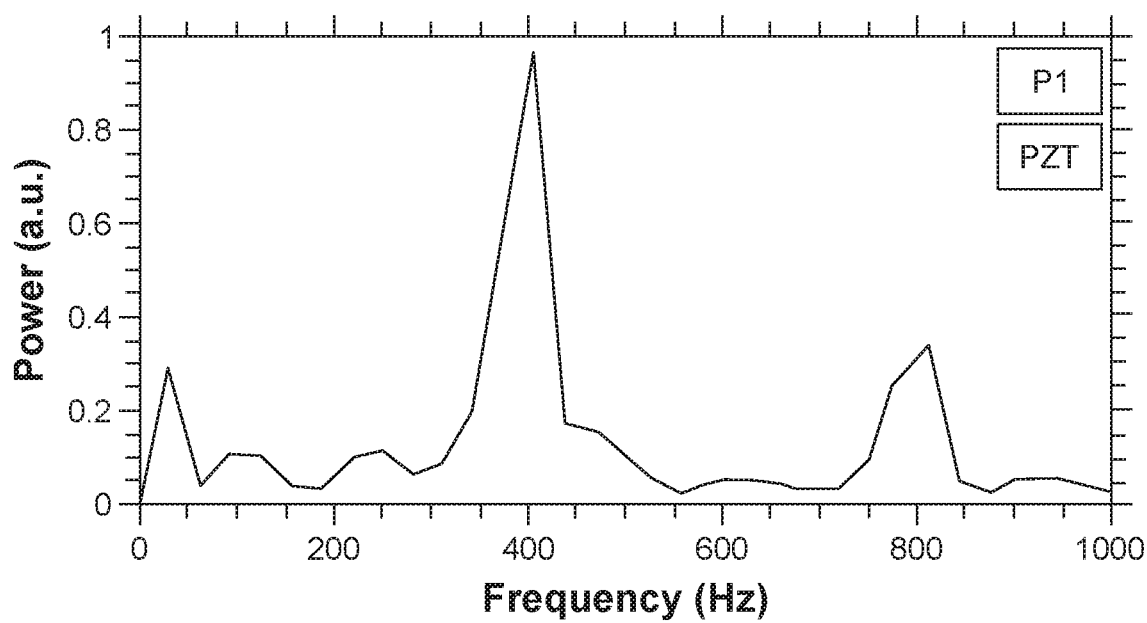
Figure 10C:
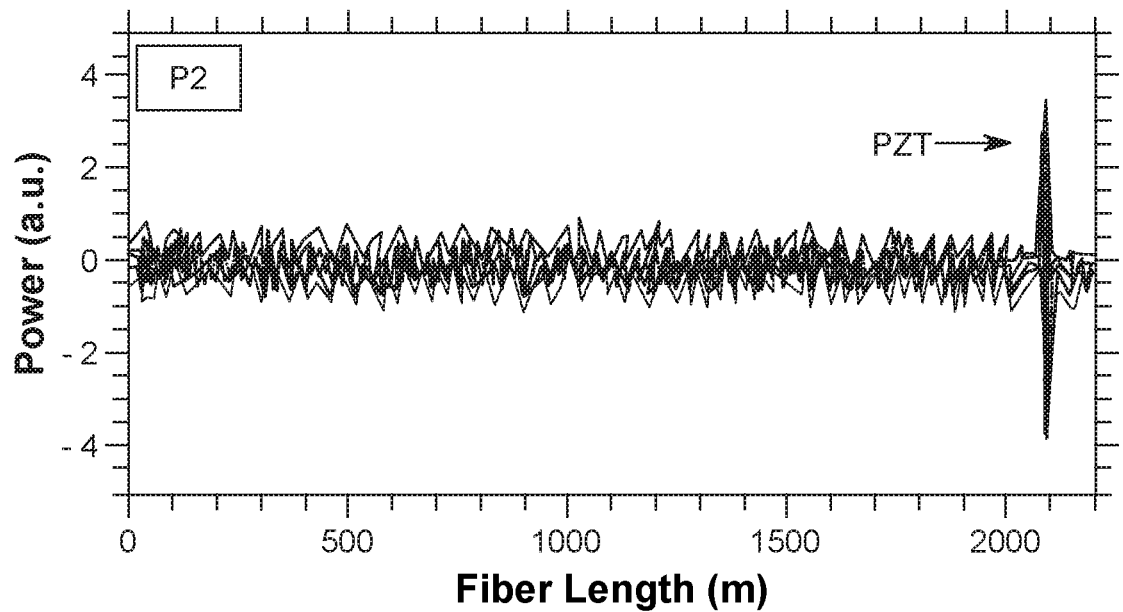
Figure 10D:
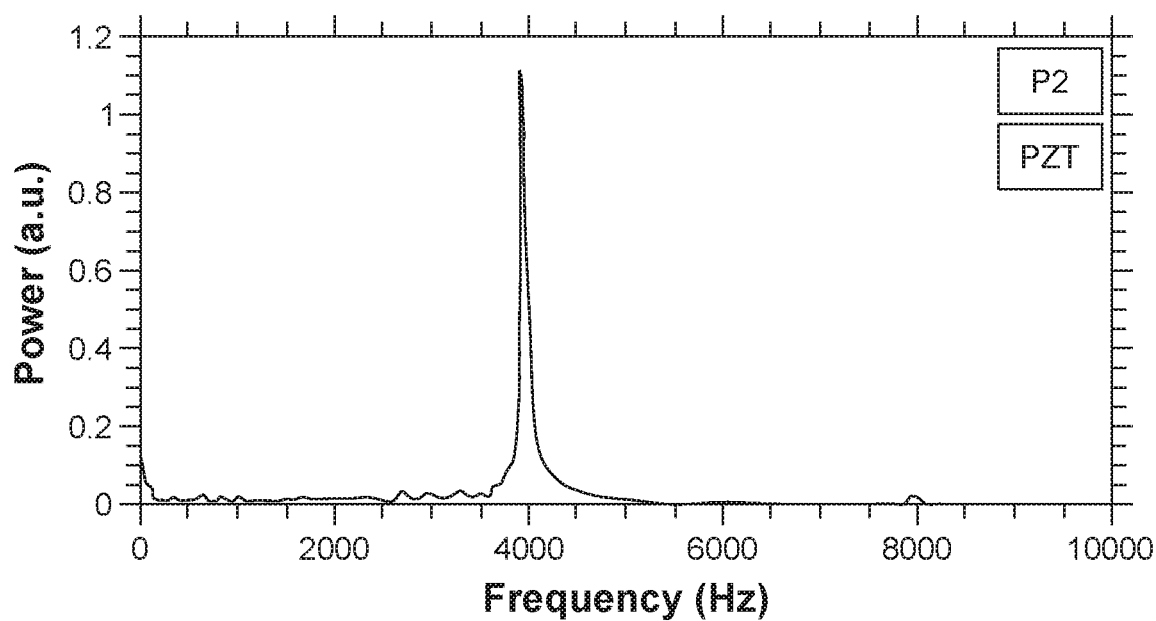

The fiber optic DAS systems 200 and 900 are generally used to detect a location along the fiber subjected to vibrations and to determine the frequencies of these vibrations. The first goal is attained via subtracting the subsequent Rayleigh traces in the time domain. After identifying the vibrations location, a Fourier transform may be applied to the Rayleigh traces at that location to calculate the vibrations frequency components. For example, it is possible to start with calibrating the DAS system by using a piezoelectric transducer (PZT) cylinder as a vibrations source. The PZT cylinder is typically used in the literature for DAS calibration since its vibrations amplitude and frequency can be predetermined using a driven function generator. For this calibration, a 10 m fiber section was wound around the PZT tube at the P1 location and the PZT was driven to vibrate with a 400 Hz frequency. FIGS. 10A and 10B show the position information and power spectrum, respectively, of this vibrations event. The results of these figures clearly indicate the ability of the DAS system to locate vibrations position and to determine their frequencies. The appearance of high-order harmonics (at 800 Hz) in the vibrations power spectrum in FIG. 10A is due to the nonlinearity of the direct detection system. Also the low-frequency noise (<100 Hz) in the power spectrum in FIG. 10B is attributed to the inevitable mechanical vibrations in our lab. For further verification, the fiber section was attached to the PZT at the P2 location when it is vibrating with 4 kHz frequency. FIGS. 10C and 10D demonstrate the successful determination of the vibrations position and frequency, respectively.

Figure 10E:
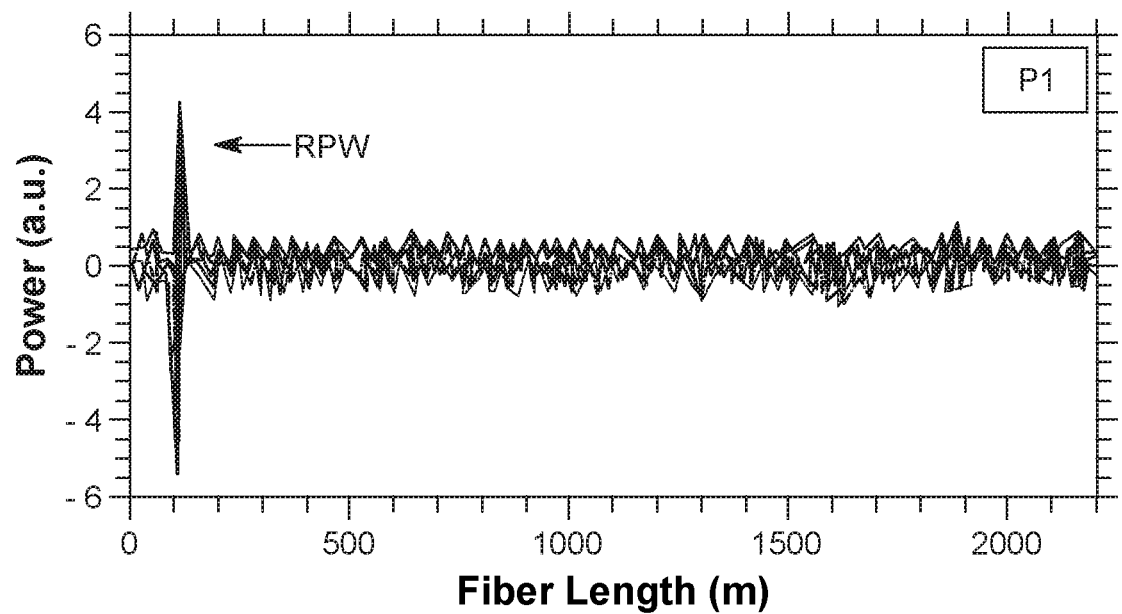
Figure 10F:
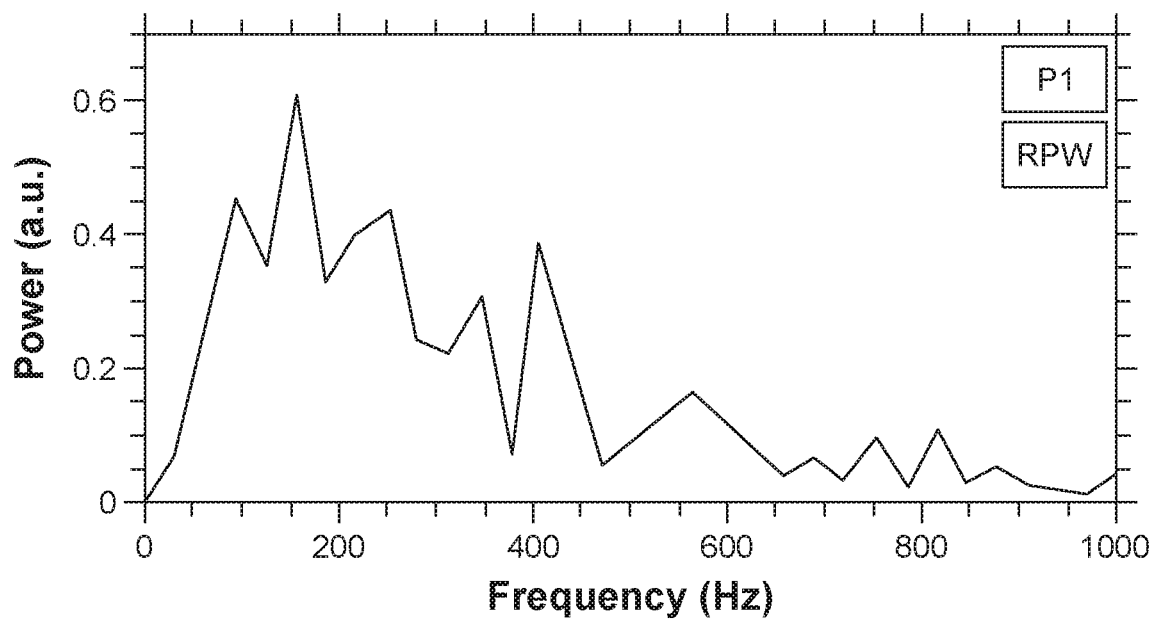
Figure 10G:
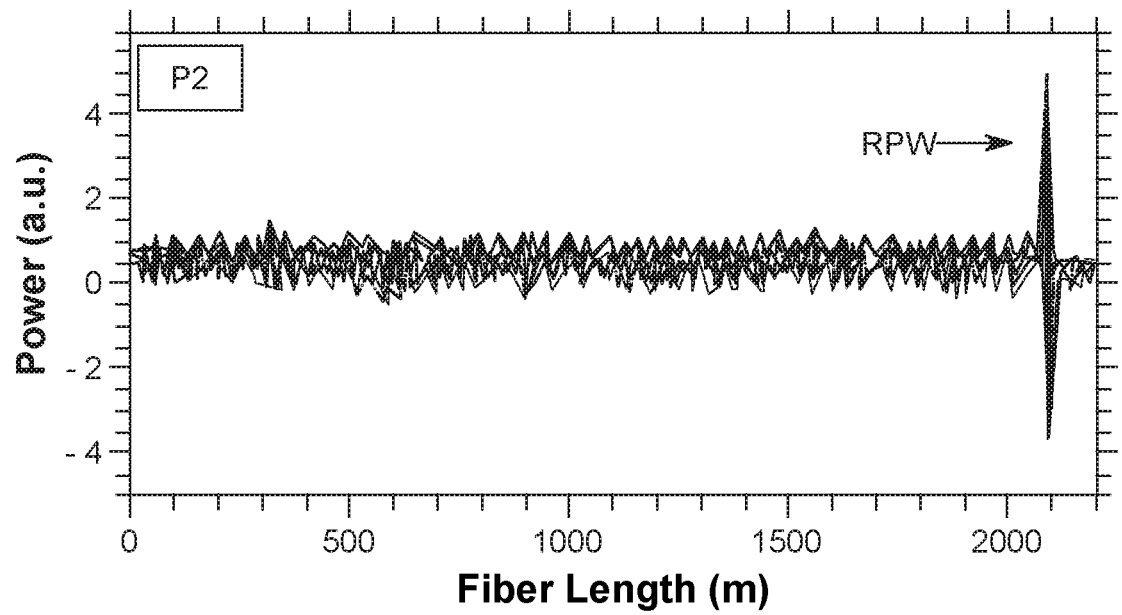
Figure 10H:
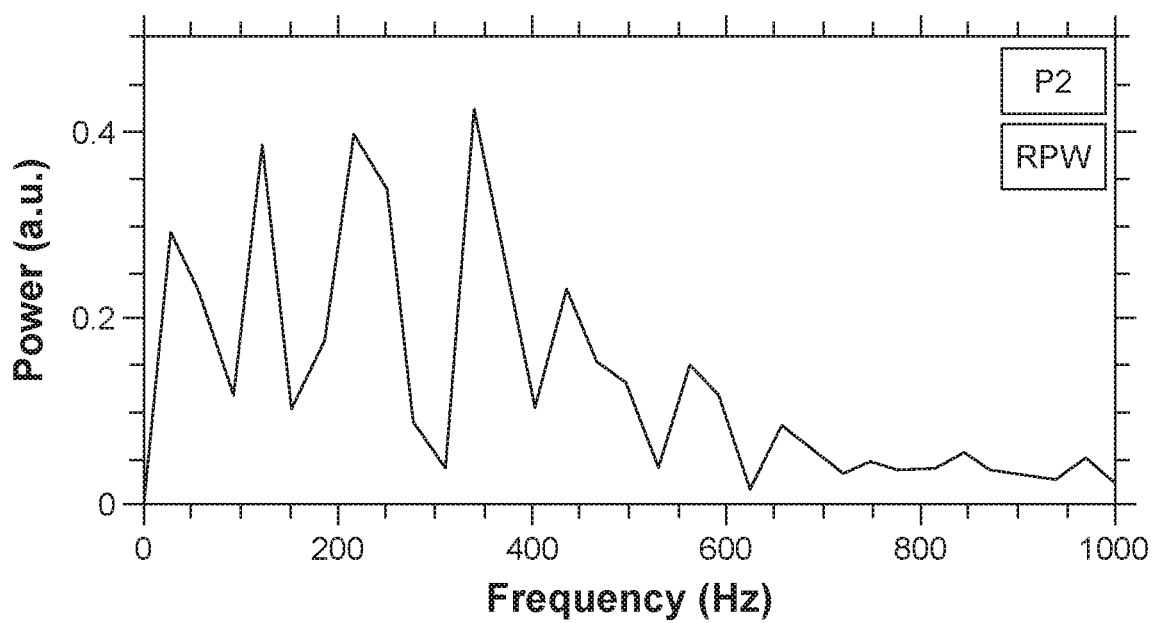

Next, the first loudspeaker was used to play the RPW sound, without generating any kind of noises (bird sounds or fan air). Representative example of the position information and power spectrum of detecting the RPW sound at P1 location are shown in FIGS. 10E and 10F, respectively. At the P2 location, similarly, the DAS system can identify the location of the RPW sound (see FIG. 10G) and determine its corresponding frequencies (see FIG. 10H). Based on the results shown in FIGS. 10F and 10G, one can conclude that the RPW sound has frequency components at about 600 Hz and thus, in a real implementation, this frequency should be used for the identification of the RPW.

Next, the experiment run only the stand fan and keep the first and second loudspeakers off to sense the frequencies of the tree swinging. The swinging position information along with its frequencies at P1/P2 location were determined. From the recorded data, it was observed that the trees swing with low frequencies (<200 Hz). As a last control experiment, the second loudspeaker LS2 was activated to produce the bird sound around the tree, when the fiber is attached to it. The DAS system did not sense the vibrations produced by the bird sounds at P1/P2. Thus, because there is no direct contact between the second loudspeaker and the fiber, the mechanical waves, transferred through air from the second loudspeaker to the fiber, are not strong enough to perturb the refractive index of the fiber core. As a result, the DAS system only detects the low frequencies noises for P1/P2 positions.

The results of this experiment indicate that in the presence of the RPW sound and other noise sources (wind and birds sound), one can separate the RPW sound by applying a high-pass filter with a 200 Hz cutoff frequency on the time-domain of the recorded Rayleigh traces.

Figure 11:
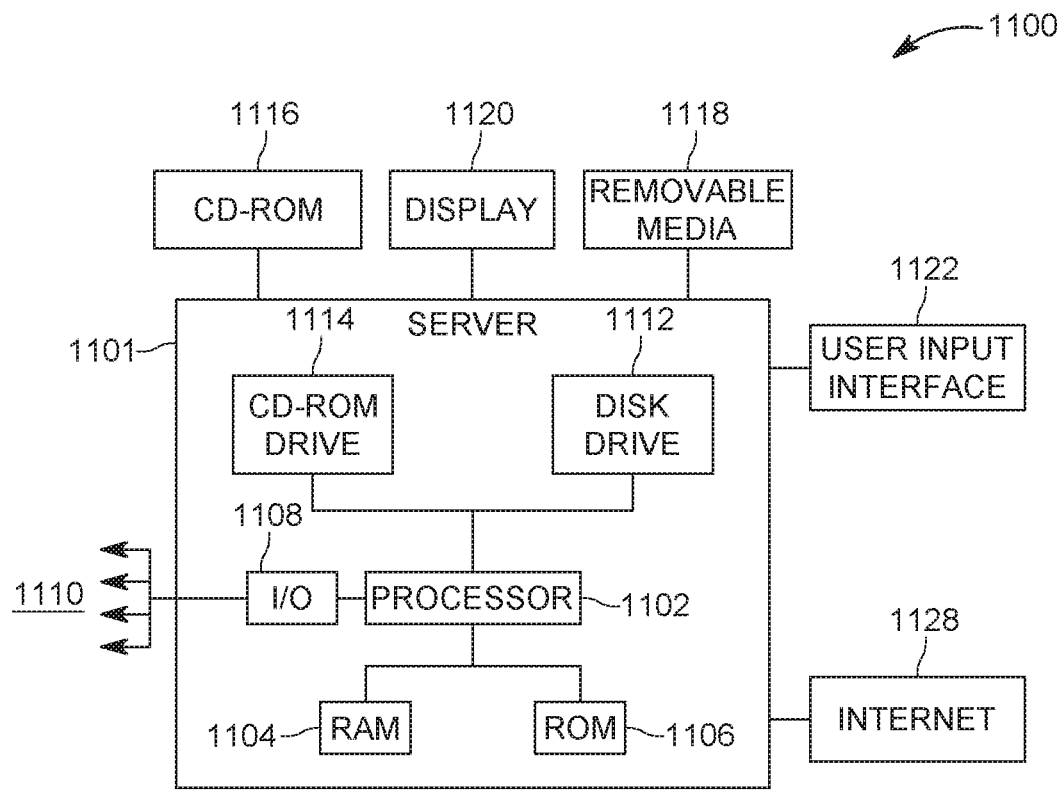
FIG. 11 is a schematic diagram of a controller that determines the presence of the RPW in a tree.

The above-discussed procedures and methods may be implemented in a computing device or controller as illustrated in FIG. 11. Hardware, firmware, software or a combination thereof may be used to perform the various steps and operations described herein. Computing device 1100 of FIG. 11 is an exemplary computing structure that may be used in connection with such a system. In one application, computing device 211 shown in FIG. 2 or computing device 954 shown in FIG. 9 can be implemented as the computing device 1100.

Exemplary computing device 1100 suitable for performing the activities described in the exemplary embodiments may include a server 1101. Such a server 1101 may include a central processor (CPU) 1102 coupled to a random access memory (RAM) 1104 and to a read-only memory (ROM) 1106. ROM 1106 may also be other types of storage media to store programs, such as programmable ROM (PROM), erasable PROM (EPROM), etc. Processor 1102 may communicate with other internal and external components through input/output (I/O) circuitry 1108 and bussing 1110 to provide control signals and the like. Processor 1102 carries out a variety of functions as are known in the art, as dictated by software and/or firmware instructions. For example, bussing 1110 may be connected to the optical fiber 220 shown in FIG. 2 or FIG. 9.

Server 1101 may also include one or more data storage devices, including hard drives 1112, CD-ROM drives 1114 and other hardware capable of reading and/or storing information, such as DVD, etc. In one embodiment, software for carrying out the above-discussed steps may be stored and distributed on a CD-ROM or DVD 1116, a USB storage device 1118 or other form of media capable of portably storing information. These storage media may be inserted into, and read by, devices such as CD-ROM drive 1114, disk drive 1112, etc. Server 1101 may be coupled to a display 1120, which may be any type of known display or presentation screen, such as LCD, plasma display, cathode ray tube (CRT), etc. A user input interface 1122 is provided, including one or more user interface mechanisms such as a mouse, keyboard, microphone, touchpad, touch screen, voice-recognition system, etc.

Server 1101 may be coupled to other devices, such as a smart device, e.g., a phone, tv set, computer, etc. The server may be part of a larger network configuration as in a global area network (GAN) such as the Internet 1128, which allows ultimate connection to various landline and/or mobile computing devices.

The disclosed embodiments provide methods and mechanisms for detecting RPWs in a tree. It should be understood that this description is not intended to limit the invention. On the contrary, the embodiments are intended to cover alternatives, modifications and equivalents, which are included in the spirit and scope of the invention as defined by the appended claims. Further, in the detailed description of the embodiments, numerous specific details are set forth in order to provide a comprehensive understanding of the claimed invention. However, one skilled in the art would understand that various embodiments may be practiced without such specific details.

Although the features and elements of the present embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

What is claimed is:

1. An optical fiber distributed acoustic sensor (DAS) system for detecting a red palm weevil and/or its larvae inside a tree, the system comprising:
   an optical fiber that is configured to be placed next to a tree; and
   a DAS box optically connected to the optical fiber and configured to receive a reflected light from the optical fiber,
   wherein the DAS box includes electronics that extracts from the reflected light a frequency in a range of [400 Hz, 4 kHz], and sends a message indicating a presence of the red palm weevil and/or its larvae inside the tree.

2. The system of claim 1, wherein the optical fiber is 10 km long.

3. The system of claim 1, wherein the optical fiber is wound around the tree.

4. The system of claim 1, wherein the optical fiber is wound around a pole and the pole is inserted into the tree.

5. The system of claim 1, wherein the optical fiber is wound around plural trees.

6. The system of claim 1, wherein the optical fiber is wound around a tree, starting at 0.5 m above the ground.

7. The system of claim 6, wherein the optical fiber is wound around the tree up to 2 m above the ground.

8. The system of claim 1, further comprising:
   additional optical fibers, each additional optical fiber being wound around plural trees; and
   an optical switch that connects the additional optical fibers to the DAS box.

9. The system of claim 8, wherein each optical fiber of the additional optical fibers is connected for a limited time period, each day, to the DAS box.

10. The system of claim 9, wherein the limited time period is an hour.

11. The system of claim 1, wherein the DAS box comprises:
    a coherent light source;
    a light modulator that modulates a continuous light, emitted by the coherent light source, to generate optical pulses;
    a function generator that modulates the continuous light;
    an amplifier to amplify the optical pulses; and
    a circulator optically connected to the light modulator and to the optical fiber.

12. The system of claim 11, wherein the DAS box further comprises:
    a photo-detector optically connected to the circulator and configured to record a signal indicative of the reflected light;
    an analog to digital converter configured to digitize the signal; and a digital signal processor configured to extract the frequency in the range of [400 Hz, 4 kHz].

13. The system of claim 12, further comprising:
a computing device that generates the message based on information from the digital signal processor.

14. The system of claim 13, further comprising:
a power supply; and
an antenna for wireless communication.

15. A method for detecting a red palm weevil inside a tree, the method comprising:
deploying an optical fiber next to a tree;
optically connecting a DAS box to the optical fiber;
receiving reflected light from the optical fiber, wherein the reflected light contains information about a sound generated by the red palm weevil;
processing with electronics in the DAS box the reflected light, to extract a frequency in a range of [400 Hz, 4 kHz], which is indicative of the red palm weevil; and
sending a message indicating a presence of the red palm weevil inside the tree.

16. The method of claim 15, wherein the optical fiber is 10 km long and a portion of the optical fiber is wound around the tree.

17. The method of claim 15, further comprising:
looping the optical fiber around a pole; and
attaching the pole to the tree.

18. The method of claim 15, further comprising:
looping the optical fiber around plural trees, for each tree starting at 0.5 m above the ground and stopping 2 m above the ground.

19. The method of claim 15, further comprising:
looping additional optical fibers around plural trees; and
connecting the additional optical fibers to the DAS box with an optical switch.

20. The method of claim 19, further comprising:
connecting each optical fiber of the additional optical fibers for a limited time period, each day, to the DAS box.

* * * * *